(12) United States Patent
Barraud et al.

(10) Patent No.: US 11,806,502 B2
(45) Date of Patent: Nov. 7, 2023

(54) MICROPUMP

(71) Applicant: Tandem Diabetes Care Switzerland Sàrl, St-Sulpice (CH)

(72) Inventors: Antoine Barraud, Lonay (CH); Simon Kuenzi, Lausanne (CH); Remy Rysman, Lausanne (CH)

(73) Assignee: Tandem Diabetes Care Switzerland Sarl, St-Sulpice (CH)

( * ) Notice: Subject to any disclaimer, the term of this patent is extended or adjusted under 35 U.S.C. 154(b) by 368 days.

(21) Appl. No.: 15/777,284

(22) PCT Filed: Nov. 15, 2016

(86) PCT No.: PCT/IB2016/056870
§ 371 (c)(1),
(2) Date: May 18, 2018

(87) PCT Pub. No.: WO2017/085624
PCT Pub. Date: May 26, 2017

(65) Prior Publication Data
US 2018/0339102 A1    Nov. 29, 2018

(30) Foreign Application Priority Data
Nov. 20, 2015 (EP) ..................................... 15195733

(51) Int. Cl.
*A61M 5/142* (2006.01)
*F04B 43/00* (2006.01)
(Continued)

(52) U.S. Cl.
CPC .... *A61M 5/14248* (2013.01); *A61M 5/14224* (2013.01); *A61M 5/16813* (2013.01);
(Continued)

(58) Field of Classification Search
CPC .......... A61M 5/14248; A61M 5/14244; A61M 5/14224; A61M 2005/14268;
(Continued)

(56) References Cited

U.S. PATENT DOCUMENTS 2,105,200 A * 1/1938 Phelps .................. F04B 43/082
417/474
2,412,397 A * 12/1946 Harper .................. F04B 43/082
417/474
(Continued)

FOREIGN PATENT DOCUMENTS

CA      2987866 A1      3/2012
DE   102013111800 A1   4/2015
(Continued)

OTHER PUBLICATIONS

Kristin Lewotsky, Tutorial: The Basics of Stepper Motors—Part I, Feb. 12, 2014 (Year: 2014).*
(Continued)

*Primary Examiner* — Kami A Bosworth
*Assistant Examiner* — Antarius S Daniel
(74) *Attorney, Agent, or Firm* — Eversheds Sutherland (US) LLP; Christopher C. Bolten; Robert D. Ward

(57) ABSTRACT

Micropump (10) including a support structure (14), a pump tube (16), and an actuation system (18) comprising one or more pump chamber actuators (28), the pump tube comprising a pump chamber portion (24) defining therein a pump chamber (26), an inlet portion (20) for inflow of fluid into the pump chamber, and an outlet portion (22) for outflow of fluid from the pump chamber. The inlet, outlet and pump chamber portions form part of a continuous section of tube made of a supple material. The one or more pump chamber actuators are configured to bias against the pump chamber portion to expel liquid contained in the pump
(Continued)

chamber via the outlet portion, respectively to bias away from the pump chamber portion to allow liquid to enter the pump chamber via the inlet portion. The pump chamber portion has a cross-sectional area Ap in an expanded state that is larger than a cross-sectional area Ai of the pump tube at the inlet and outlet portions.

27 Claims, 9 Drawing Sheets

(51) Int. Cl.
<table>
<tr><td>F04B 43/09</td><td>(2006.01)</td></tr>
<tr><td>F04B 43/04</td><td>(2006.01)</td></tr>
<tr><td>F04B 19/00</td><td>(2006.01)</td></tr>
<tr><td>F04B 43/14</td><td>(2006.01)</td></tr>
<tr><td>A61M 5/168</td><td>(2006.01)</td></tr>
<tr><td>F04B 49/22</td><td>(2006.01)</td></tr>
<tr><td>F04B 53/10</td><td>(2006.01)</td></tr>
<tr><td>B29C 69/02</td><td>(2006.01)</td></tr>
<tr><td>B29K 27/12</td><td>(2006.01)</td></tr>
<tr><td>B29L 31/00</td><td>(2006.01)</td></tr>
</table>

(52) U.S. Cl.
CPC ........ *F04B 19/006* (2013.01); *F04B 43/0072* (2013.01); *F04B 43/043* (2013.01); *F04B 43/09* (2013.01); *F04B 43/095* (2013.01); *F04B 43/14* (2013.01); *F04B 49/22* (2013.01); *F04B 53/1072* (2013.01); *A61M 2005/14268* (2013.01); *A61M 2205/3317* (2013.01); *A61M 2207/00* (2013.01); *B29C 69/02* (2013.01); *B29K 2027/12* (2013.01); *B29L 2031/7496* (2013.01)

(58) Field of Classification Search
CPC .. F04B 19/006; F04B 43/0072; F04B 43/043; F04B 43/095; F04B 43/09; F04B 49/22; F16K 7/00; F16K 7/066; F16K 7/02; F16K 7/04; F16K 7/06
See application file for complete search history.

(56) References Cited

U.S. PATENT DOCUMENTS

| | | | |
|---|---|---|---|
| 3,609,069 A * | 9/1971 | Martinelli | F04B 43/082 417/474 |
| 4,042,153 A * | 8/1977 | Callahan | B01J 2/02 222/207 |
| 4,199,307 A * | 4/1980 | Jassawalla | A61M 5/14224 128/DIG. 12 |
| 4,218,416 A | 8/1980 | Gokcen | |
| 4,236,880 A | 12/1980 | Archibald | |
| 4,273,121 A * | 6/1981 | Jassawalla | A61M 5/14224 604/153 |
| 4,290,346 A | 9/1981 | Bujan | |
| 4,322,201 A * | 3/1982 | Archibald | F04B 7/00 417/279 |
| 4,410,322 A | 10/1983 | Archibald | |
| 4,482,347 A * | 11/1984 | Borsanyi | A61M 5/14244 417/474 |
| 4,493,704 A | 1/1985 | Beard et al. | |
| 4,501,405 A * | 2/1985 | Usry | F04B 43/09 417/474 |
| 4,596,575 A | 6/1986 | Rosenberg et al. | |
| 4,616,802 A | 10/1986 | Tseng et al. | |
| 4,617,014 A | 10/1986 | Cannon et al. | |
| 4,657,490 A | 4/1987 | Abbott | |
| 4,854,836 A * | 8/1989 | Borsanyi | F04B 43/0072 417/474 |
| 4,934,372 A | 6/1990 | Corenman et al. | |
| 5,056,992 A | 10/1991 | Simons et al. | |
| 5,066,278 A | 11/1991 | Hirschberg et al. | |
| 5,088,522 A | 2/1992 | Rath et al. | |
| 5,137,023 A | 8/1992 | Mendelson et al. | |
| 5,217,355 A | 6/1993 | Hyman et al. | |
| 5,252,044 A * | 10/1993 | Raines | F04B 43/021 417/479 |
| 5,318,546 A | 6/1994 | Bierman | |
| 5,482,446 A | 1/1996 | Williamson et al. | |
| 5,637,095 A | 6/1997 | Nason et al. | |
| 5,851,197 A | 12/1998 | Marano et al. | |
| 5,964,583 A | 10/1999 | Danby | |
| 6,093,172 A | 7/2000 | Funderburk et al. | |
| 6,165,151 A | 12/2000 | Weiner | |
| 6,293,925 B1 | 9/2001 | Safabash et al. | |
| 6,607,509 B2 | 8/2003 | Bobroff et al. | |
| 6,723,077 B2 | 4/2004 | Pickup et al. | |
| 6,801,420 B2 | 10/2004 | Talbot et al. | |
| 6,830,562 B2 | 12/2004 | Mogensen et al. | |
| 6,881,043 B2 | 4/2005 | Barak | |
| 7,137,964 B2 | 11/2006 | Flaherty | |
| 7,204,823 B2 | 4/2007 | Estes et al. | |
| 7,315,753 B2 | 1/2008 | Baker, Jr. et al. | |
| 7,329,239 B2 | 2/2008 | Safabash et al. | |
| 7,356,364 B1 | 4/2008 | Bullock et al. | |
| 7,879,023 B2 | 2/2011 | Wood, Jr. | |
| 7,879,026 B2 | 2/2011 | Estes et al. | |
| 8,152,771 B2 | 4/2012 | Mogensen et al. | |
| 8,377,002 B2 * | 2/2013 | Hanson | A61M 5/003 604/533 |
| 8,657,807 B2 | 2/2014 | Blomquist | |
| 9,114,208 B2 | 8/2015 | Smith et al. | |
| 9,517,024 B2 | 12/2016 | Kiani et al. | |
| 9,610,018 B2 | 4/2017 | Gulati et al. | |
| 9,615,779 B2 | 4/2017 | Pryor et al. | |
| 9,636,457 B2 | 5/2017 | Newberry et al. | |
| 9,735,502 B2 | 8/2017 | Stevens et al. | |
| 9,735,893 B1 | 8/2017 | Aleksov et al. | |
| 9,820,691 B2 | 11/2017 | Kiani | |
| 9,833,152 B2 | 12/2017 | Kiani et al. | |
| 9,931,065 B2 | 4/2018 | Pryor et al. | |
| 9,967,040 B2 | 5/2018 | Aleksov et al. | |
| 9,980,140 B1 | 5/2018 | Spencer et al. | |
| 9,993,595 B2 | 6/2018 | Michaud et al. | |
| 10,137,245 B2 | 11/2018 | Melker et al. | |
| 10,278,732 B2 | 5/2019 | Schoonmaker et al. | |
| 10,279,106 B1 | 5/2019 | Cook et al. | |
| 10,398,320 B2 | 9/2019 | Kiani et al. | |
| 10,518,069 B2 | 12/2019 | Boden, Jr. et al. | |
| 11,139,754 B1 | 10/2021 | Shi et al. | |
| 11,241,530 B1 | 2/2022 | Fridez et al. | |
| 11,529,460 B1 | 12/2022 | Pruijs et al. | |
| 2002/0001530 A1 | 1/2002 | Doi et al. | |
| 2002/0071225 A1 | 6/2002 | Sheldon et al. | |
| 2002/0091358 A1 | 7/2002 | Klitmose | |
| 2002/0169439 A1 | 11/2002 | Flaherty | |
| 2004/0064088 A1 | 4/2004 | Gorman et al. | |
| 2004/0082920 A1 | 4/2004 | Mori et al. | |
| 2004/0092873 A1 | 5/2004 | Moberg | |
| 2004/0158207 A1 | 8/2004 | Hunn et al. | |
| 2005/0043687 A1 | 2/2005 | Mogensen et al. | |
| 2005/0101912 A1 | 5/2005 | Faust et al. | |
| 2005/0124936 A1 | 6/2005 | Mogensen et al. | |
| 2005/0277887 A1 | 12/2005 | Douglas et al. | |
| 2006/0036214 A1 | 2/2006 | Mogensen et al. | |
| 2007/0060874 A1 | 3/2007 | Nesbitt et al. | |
| 2007/0191772 A1 | 8/2007 | Wojcik | |
| 2007/0191773 A1 | 8/2007 | Wojcik | |
| 2007/0219496 A1 | 9/2007 | Kamen et al. | |
| 2008/0051727 A1 | 2/2008 | Moberg et al. | |
| 2008/0091175 A1 | 4/2008 | Frikart et al. | |
| 2008/0097289 A1 | 4/2008 | Steil et al. | |
| 2008/0281290 A1 | 11/2008 | Yodfat et al. | |
| 2008/0319414 A1 | 12/2008 | Yodfat et al. | |
| 2009/0069750 A1 | 3/2009 | Schraga | |
| 2009/0118667 A1 | 5/2009 | Haueter et al. | |
| 2009/0177146 A1 | 7/2009 | Nesbitt et al. | |
| 2010/0004598 A1 | 1/2010 | Eberhart et al. | |
| 2010/0017141 A1 | 1/2010 | Campbell et al. | |
| 2010/0064236 A1 | 3/2010 | Buck et al. | |

(56) References Cited

U.S. PATENT DOCUMENTS

| | | |
|---|---|---|
| 2010/0064257 A1 | 3/2010 | Buck et al. |
| 2010/0077198 A1 | 3/2010 | Buck et al. |
| 2010/0082167 A1 | 4/2010 | Haueter et al. |
| 2010/0106082 A1* | 4/2010 | Zhou .............. A61M 5/14232 604/67 |
| 2010/0174239 A1* | 7/2010 | Yodfat .................. B32B 1/08 604/153 |
| 2010/0211011 A1 | 8/2010 | Haar |
| 2010/0228226 A1 | 9/2010 | Nielsen |
| 2011/0054439 A1 | 3/2011 | Yodfat et al. |
| 2011/0137297 A1 | 6/2011 | Kiani et al. |
| 2011/0152769 A1 | 6/2011 | Ramey et al. |
| 2011/0152770 A1 | 6/2011 | DiPerna et al. |
| 2011/0218495 A1 | 9/2011 | Remde |
| 2011/0247397 A1 | 10/2011 | Friedli et al. |
| 2011/0266999 A1 | 11/2011 | Yodfat et al. |
| 2012/0051946 A1 | 3/2012 | Lee et al. |
| 2012/0059348 A1 | 3/2012 | Haueter et al. |
| 2012/0078181 A1* | 3/2012 | Smith .................. H02J 7/0029 604/404 |
| 2012/0093311 A1 | 4/2012 | Nierzwick et al. |
| 2012/0093315 A1 | 4/2012 | Nierzwick et al. |
| 2012/0095393 A1 | 4/2012 | Reinke et al. |
| 2012/0150144 A1 | 6/2012 | Campbell et al. |
| 2012/0157655 A1 | 6/2012 | Yoneda et al. |
| 2012/0209187 A1 | 8/2012 | Kamen et al. |
| 2012/0220939 A1 | 8/2012 | Yodfat et al. |
| 2012/0226124 A1 | 9/2012 | Blomquist |
| 2012/0232485 A1 | 9/2012 | Blomquist |
| 2012/0232486 A1 | 9/2012 | Blomquist |
| 2012/0232521 A1 | 9/2012 | Blomquist |
| 2012/0239362 A1 | 9/2012 | Blomquist |
| 2012/0259185 A1 | 10/2012 | Yodfat et al. |
| 2012/0302991 A1 | 11/2012 | Blomquist et al. |
| 2013/0041342 A1 | 2/2013 | Bernini et al. |
| 2013/0060105 A1 | 3/2013 | Shah et al. |
| 2013/0079709 A1 | 3/2013 | Eberhart et al. |
| 2013/0245555 A1 | 9/2013 | Dirac et al. |
| 2013/0267811 A1 | 10/2013 | Pryor et al. |
| 2013/0338594 A1 | 12/2013 | Da Ros et al. |
| 2014/0128839 A1 | 5/2014 | DiIanni et al. |
| 2014/0148762 A1 | 5/2014 | Haueter et al. |
| 2014/0188516 A1 | 7/2014 | Kamen et al. |
| 2014/0249500 A1 | 9/2014 | Estes |
| 2014/0276419 A1 | 9/2014 | Rosinko et al. |
| 2014/0276420 A1 | 9/2014 | Rosinko |
| 2014/0276574 A1 | 9/2014 | Saint |
| 2014/0288399 A1 | 9/2014 | Regittnig |
| 2014/0378898 A1 | 12/2014 | Rosinko |
| 2015/0073337 A1 | 3/2015 | Saint et al. |
| 2015/0182689 A1* | 7/2015 | Dhami .............. A61M 5/14244 604/151 |
| 2015/0182695 A1 | 7/2015 | Rosinko |
| 2015/0182697 A1 | 7/2015 | Panzer |
| 2015/0222517 A1 | 8/2015 | McLaughlin et al. |
| 2015/0265768 A1 | 9/2015 | Vazquez et al. |
| 2016/0008539 A1 | 1/2016 | Miyazaki |
| 2016/0030669 A1 | 2/2016 | Harris et al. |
| 2016/0067403 A1 | 3/2016 | Moberg et al. |
| 2016/0106910 A1 | 4/2016 | Yap et al. |
| 2016/0228641 A1 | 8/2016 | Gescheit et al. |
| 2016/0243302 A1 | 8/2016 | Gyrn |
| 2016/0254952 A1 | 9/2016 | Harvey et al. |
| 2016/0296715 A1 | 10/2016 | Clemenz et al. |
| 2016/0303333 A1 | 10/2016 | Momose |
| 2016/0339172 A1 | 11/2016 | Michaud et al. |
| 2017/0014572 A1 | 1/2017 | Newberry et al. |
| 2017/0027523 A1 | 2/2017 | Venkatraman et al. |
| 2017/0056582 A1 | 3/2017 | Niklaus |
| 2017/0072140 A1 | 3/2017 | Bazargan et al. |
| 2017/0112534 A1 | 4/2017 | Schoonmaker et al. |
| 2017/0188911 A1 | 7/2017 | Halac et al. |
| 2017/0238805 A1 | 8/2017 | Addison et al. |
| 2017/0259015 A1 | 9/2017 | Caspers |
| 2017/0274146 A1 | 9/2017 | Newberry et al. |
| 2017/0368258 A1 | 12/2017 | Fleischer |
| 2018/0000999 A1 | 1/2018 | Dolmatch et al. |
| 2018/0025120 A1 | 1/2018 | Cronrath et al. |
| 2018/0060520 A1 | 3/2018 | Degen et al. |
| 2018/0207356 A1 | 7/2018 | Joseph et al. |
| 2018/0256813 A1 | 9/2018 | Chow et al. |
| 2018/0280608 A1 | 10/2018 | Gillett et al. |
| 2018/0318550 A1 | 11/2018 | Chiu et al. |
| 2018/0333532 A1 | 11/2018 | Wei |
| 2019/0001055 A1 | 1/2019 | Gyrn |
| 2019/0083712 A1 | 3/2019 | List |
| 2019/0091404 A1 | 3/2019 | Nazzaro et al. |
| 2019/0133505 A1 | 5/2019 | Jager |
| 2019/0151568 A1 | 5/2019 | Cardinali et al. |
| 2019/0160225 A1 | 5/2019 | Verlaak et al. |
| 2019/0175818 A1 | 6/2019 | Meenken |
| 2019/0184072 A1 | 6/2019 | Madden et al. |
| 2019/0192768 A1 | 6/2019 | Gupta et al. |
| 2019/0255251 A1 | 8/2019 | DiIanni et al. |
| 2019/0351134 A1 | 11/2019 | Cook et al. |
| 2020/0016335 A1 | 1/2020 | DiPerna et al. |
| 2020/0023122 A1 | 1/2020 | McCullough et al. |
| 2020/0037891 A1 | 2/2020 | Kiani et al. |
| 2020/0069875 A1 | 3/2020 | Nazzaro et al. |
| 2020/0101219 A1 | 4/2020 | Wang et al. |
| 2020/0329433 A1 | 10/2020 | Kruse et al. |
| 2020/0360235 A1 | 11/2020 | Møller |
| 2020/0373009 A1 | 11/2020 | Shapley et al. |
| 2021/0038813 A1 | 2/2021 | O'Connor et al. |
| 2021/0093779 A1 | 4/2021 | Trachtenberg |
| 2021/0162119 A1 | 6/2021 | Barraud et al. |
| 2021/0213198 A1 | 7/2021 | Gyory |
| 2021/0272687 A1 | 9/2021 | Klopfenstein et al. |
| 2021/0280309 A1 | 9/2021 | Klopfenstein et al. |
| 2022/0226568 A1 | 7/2022 | Oberg et al. |

FOREIGN PATENT DOCUMENTS

| | | |
|---|---|---|
| DE | 102013111800 A1 | 4/2015 |
| EP | 0721358 A1 | 7/1996 |
| EP | 0721358 A1 | 7/1996 |
| EP | 1410814 A2 | 4/2004 |
| EP | 1410814 A2 | 4/2004 |
| EP | 1716879 A1 | 11/2006 |
| EP | 1716879 A1 | 11/2006 |
| EP | 1 944 150 | 7/2008 |
| EP | 2436414 A2 | 4/2012 |
| EP | 2698178 A2 | 2/2014 |
| EP | 2698178 A2 | 2/2014 |
| EP | 2852122 A1 | 3/2015 |
| GB | 2 065 789 | 7/1981 |
| WO | 1980/001934 | 9/1980 |
| WO | 0220073 A2 | 3/2002 |
| WO | WO-0220073 A2 | 3/2002 |
| WO | 2005/016534 | 2/2005 |
| WO | 2008155377 A1 | 12/2008 |
| WO | WO-2008155377 A1 | 12/2008 |
| WO | WO-2016196587 A1 | 12/2016 |
| WO | 2017085624 A1 | 5/2017 |
| WO | WO-2017085624 A1 | 5/2017 |
| WO | 2017205816 A1 | 11/2017 |
| WO | WO-2017205816 A1 | 11/2017 |
| WO | 2019110839 A1 | 6/2019 |
| WO | WO-2019110839 A1 | 6/2019 |
| WO | WO-2022107078 A1 | 5/2022 |

OTHER PUBLICATIONS

International Search Report and Written Opinion of the ISA for PCT/IB2016/056870, dated Feb. 3, 2017, 12 pages.

Accu-Check Solo, User's Manual, Accu-Check Solo micropump system, Roche Diabetes Care (2019).

Ebrahim et al., "New secure healthcare system using cloud of things", Cluster Computing, vol. 20, No. 3, May 5, 2017, pp. 2211-2229.

Fomichev et al., "Survey and Systematization of Secure Device Pairing", arxiv.org, Cornell University Library, Sep. 8, 2017.

(56) References Cited

OTHER PUBLICATIONS

International Search Report for PCT/EP2018/084069, dated Apr. 8, 2019, 7 pages.
International Search Report for PCT/EP2019/068053, dated Sep. 19, 2019, 4 pages.
International Search Report for PCT/EP2019/068054, dated Sep. 19, 2019, 4 pages.
Medtronic MiniMed (tm) 770G, System User Guide, https://www.medtronicdiabetes.com/sites/default/files/library/download-library/user-guides/MiniMed_770G_System_User_Guide.pdf (2020).
Omnipod-Insulin Management System, UST400 User Guide, https://www.omnipo.com/sites/default/files/2021-04/Omnipod-System_User-Guide_English (Apr. 2021).
Osram-Light is Wearable, Health Monitoring and Fitness Tracking, Osram Opto Semiconductors, Flyer posted online Jan. 22, 2015, file:///C:/Users/jponton/Desktop/Osram_676865_Flyer_Health_Monitoring_and_Fitness_Tracking_2016_(GB).pdf (Year: 2015).
Park, "Security Mechanism Based on Hospital Authentication Server for Secure Application of Implantable Medical Devices", Biomed Research International, vol. 2014, Jul. 24, 2014, pp. 1-12.
t:slim Insulin Pump, User Guide, Tandem Diabetes Care, https://www.tandemdiabetes.com/docs/default-source/product-documents/tslim-insulin-pump (2017).
Written Opinion of the ISA for PCT/EP2018/084069, dated Apr. 8, 2019, 9 pages.
Written Opinion of the ISA for PCT/EP2019/068053, dated Sep. 19, 2019, 7 pages.
Written Opinion of the ISA for PCT/EP2019/068054, dated Sep. 19, 2019, 9 pages.
Wu et al., "A Secure Proxy-based Access Control Scheme for Implantable Medical Devices", arxiv.org, Cornell University Library, Mar. 21, 2018.
Camara et al., "Security Mechanism Based on Hospital Authentication Server for Secure Application of Implantable Medical Devices", Journal of Biomedical Informatics, vol. 55, Jun. 1, 2015, pp. 272-289.
International Search Report & Written Opinion dated Feb. 23, 2022 in Int'l PCT Patent Appl. Serial No. PCT/IB2021/060766.
Invitation to Pay Additional Fees and Communication Relating To The Results of the Partial International Search dated Aug. 10, 2022 in Int'l PCT Patent Appl. Serial No. PCT/IB2022/054863.
International Search Report & Written Opinion dated Oct. 4, 2022 in Int'l PCT Patent Appl. Serial No. PCT/IB2022/054863.

* cited by examiner

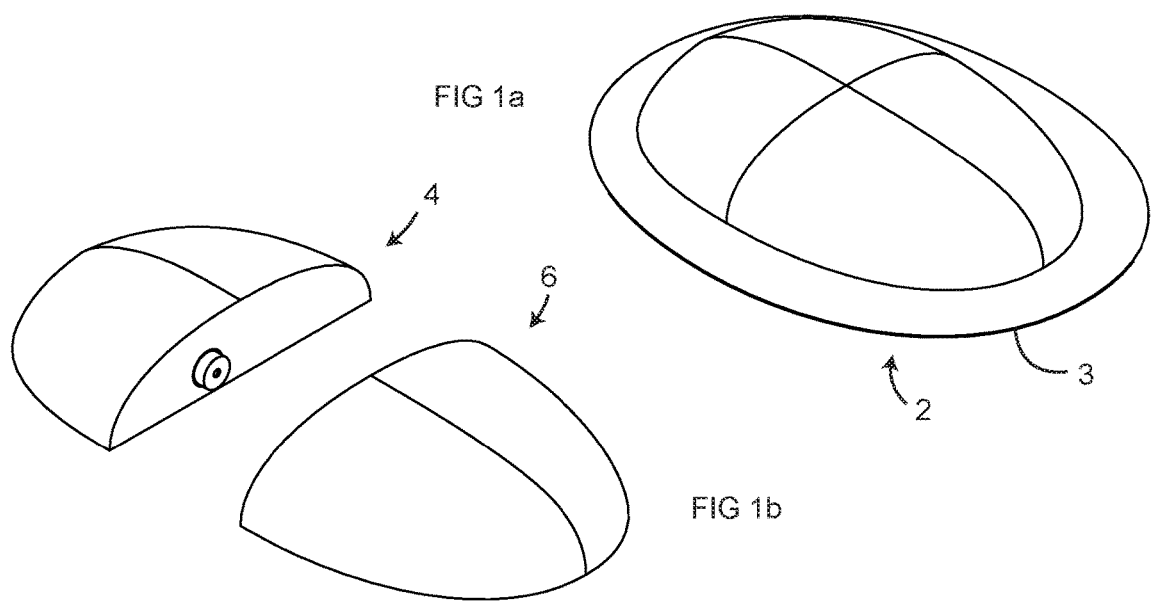
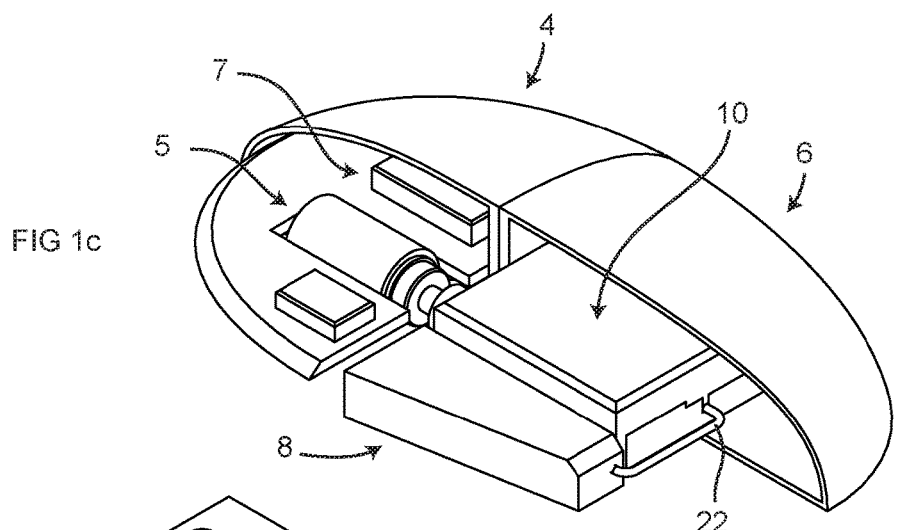
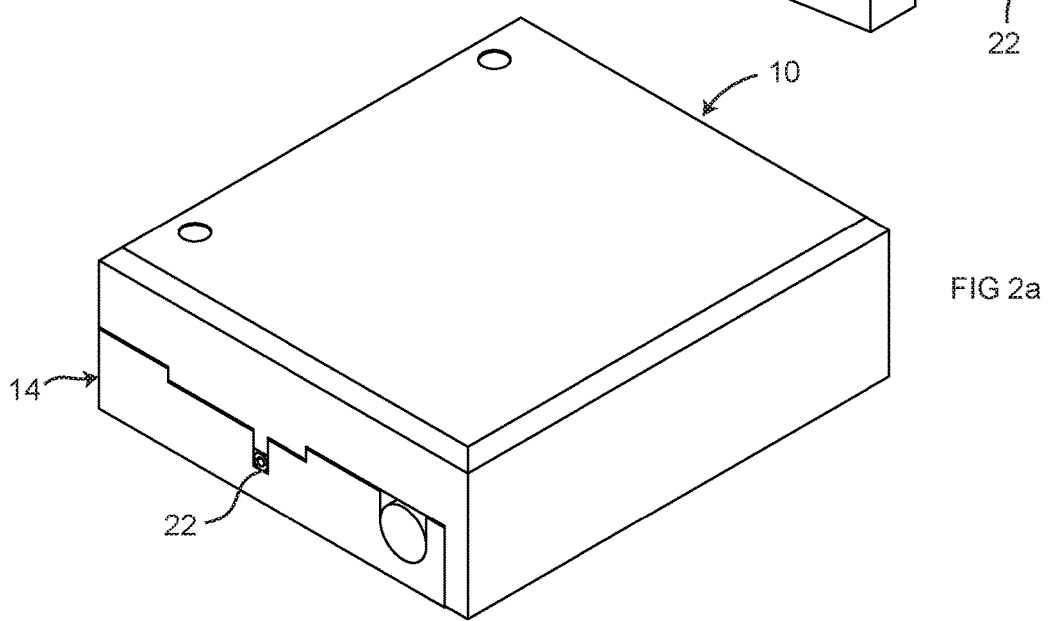

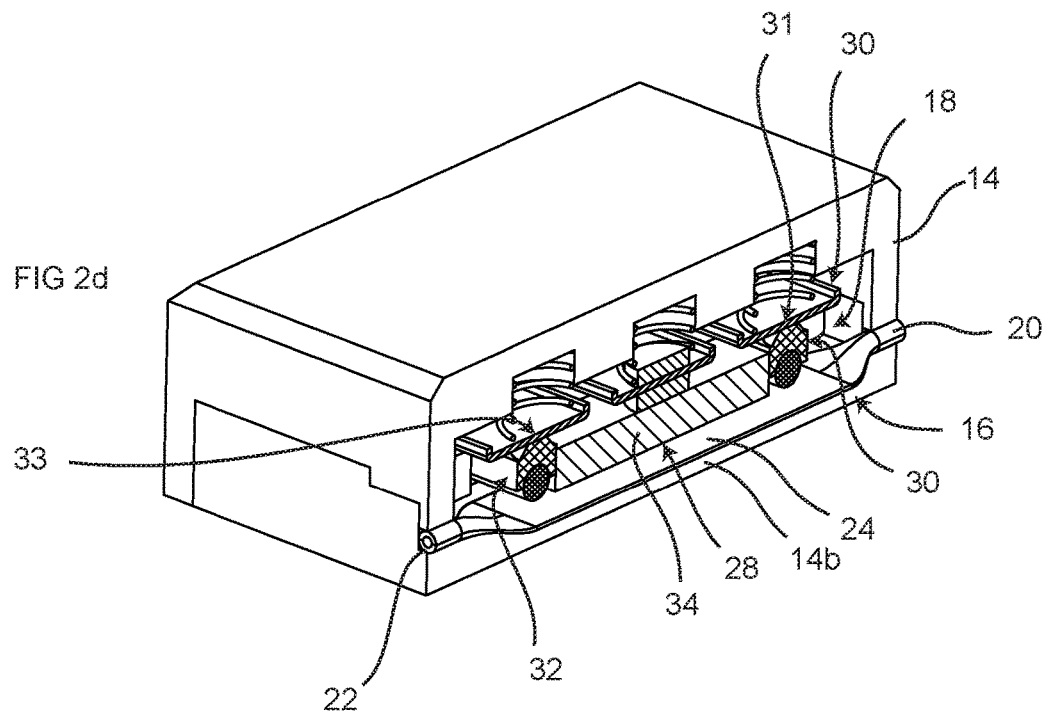
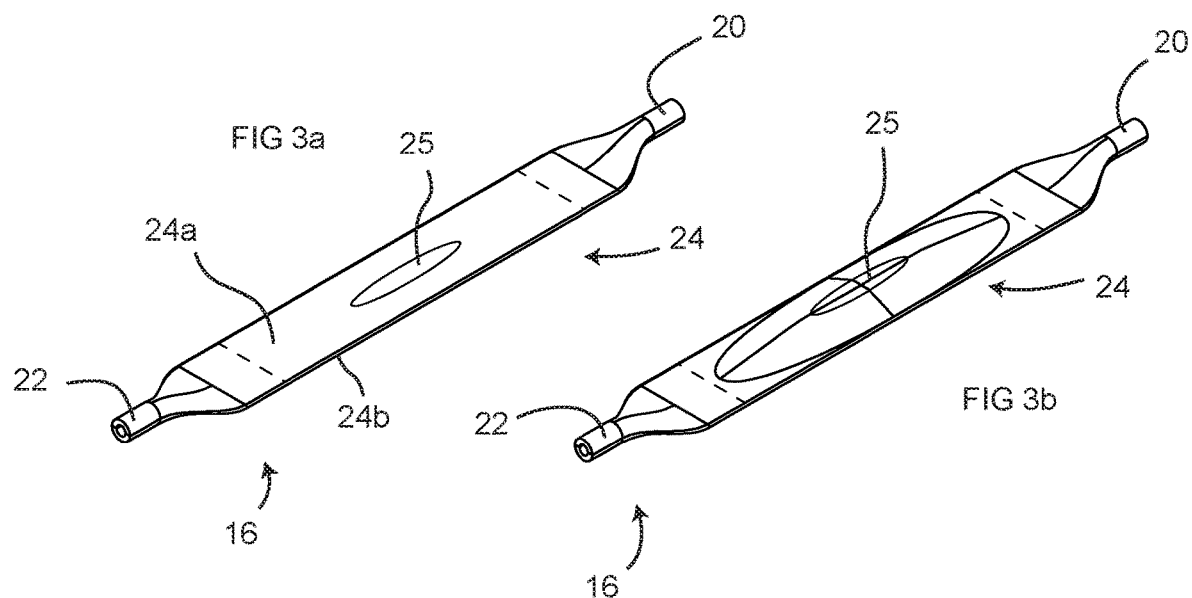

COUPE G-G

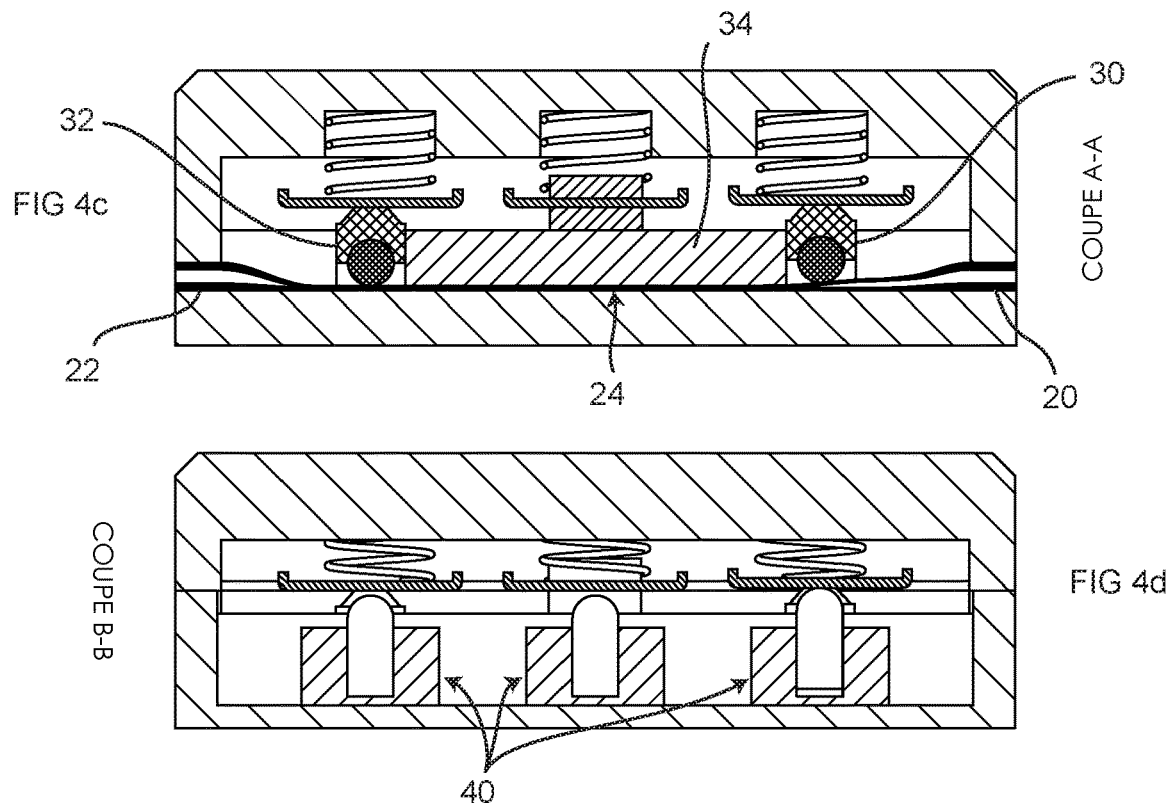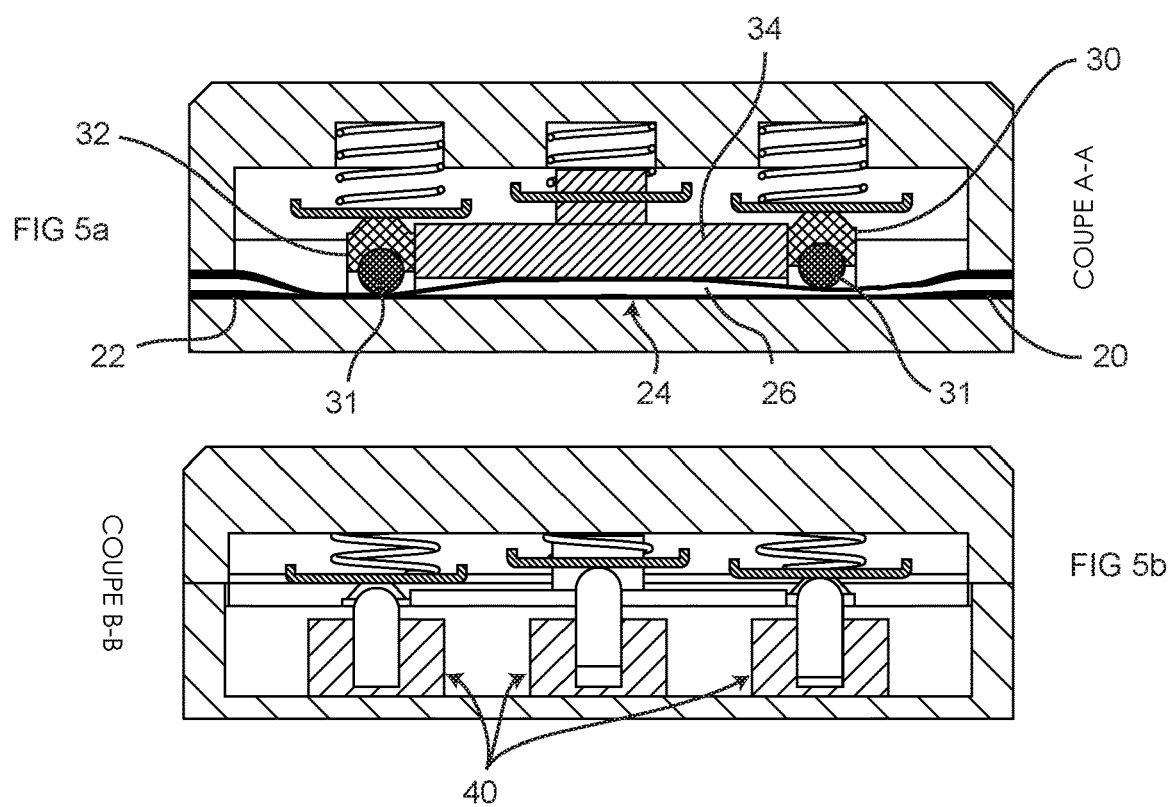

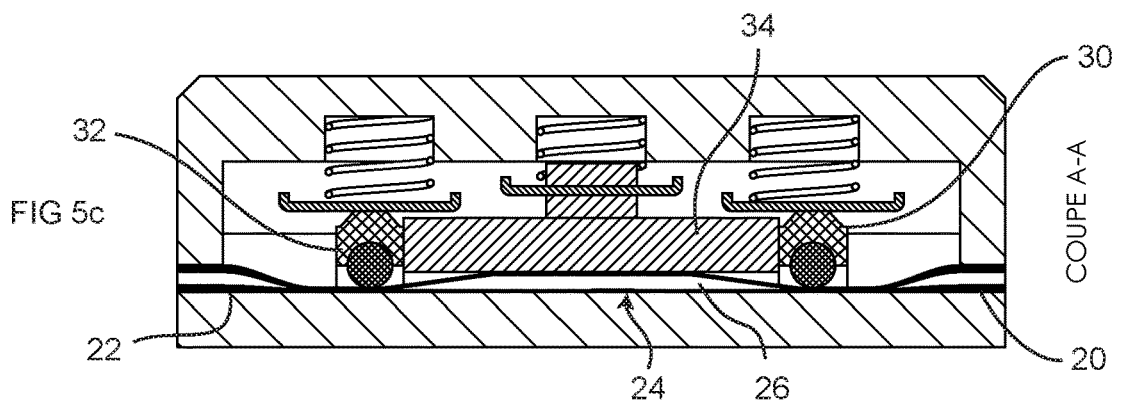
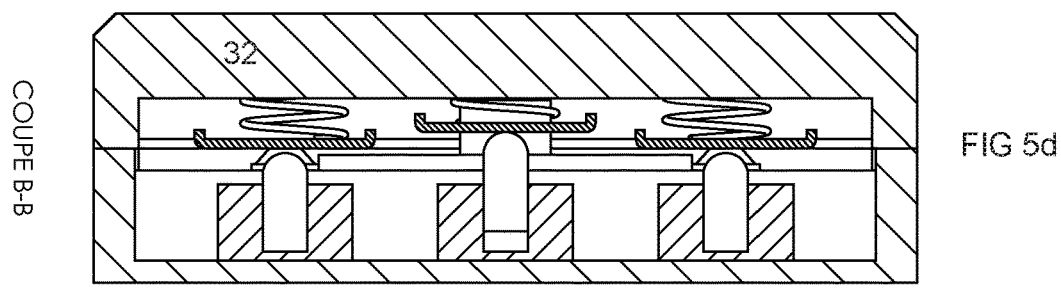
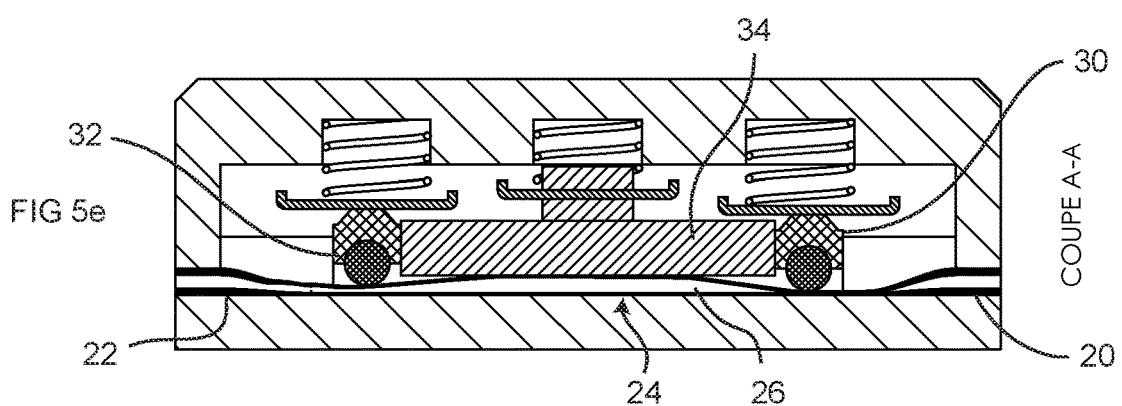
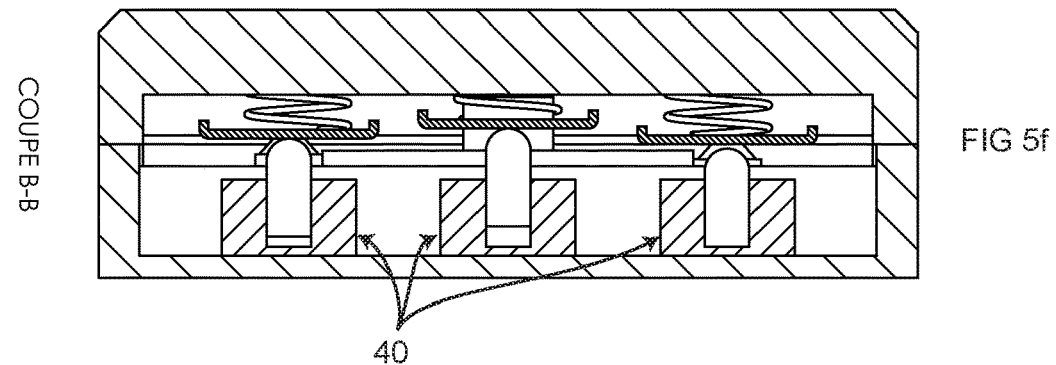

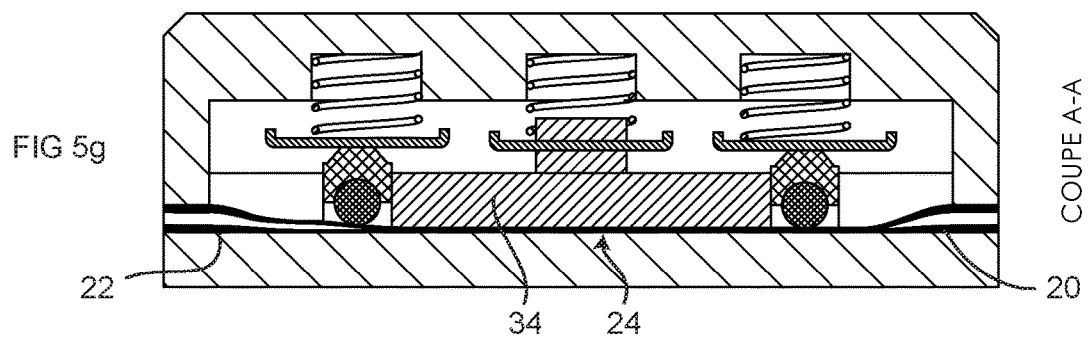
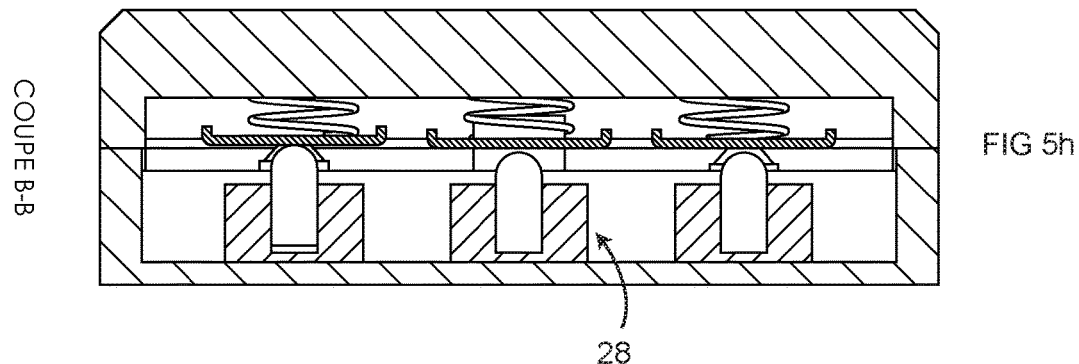
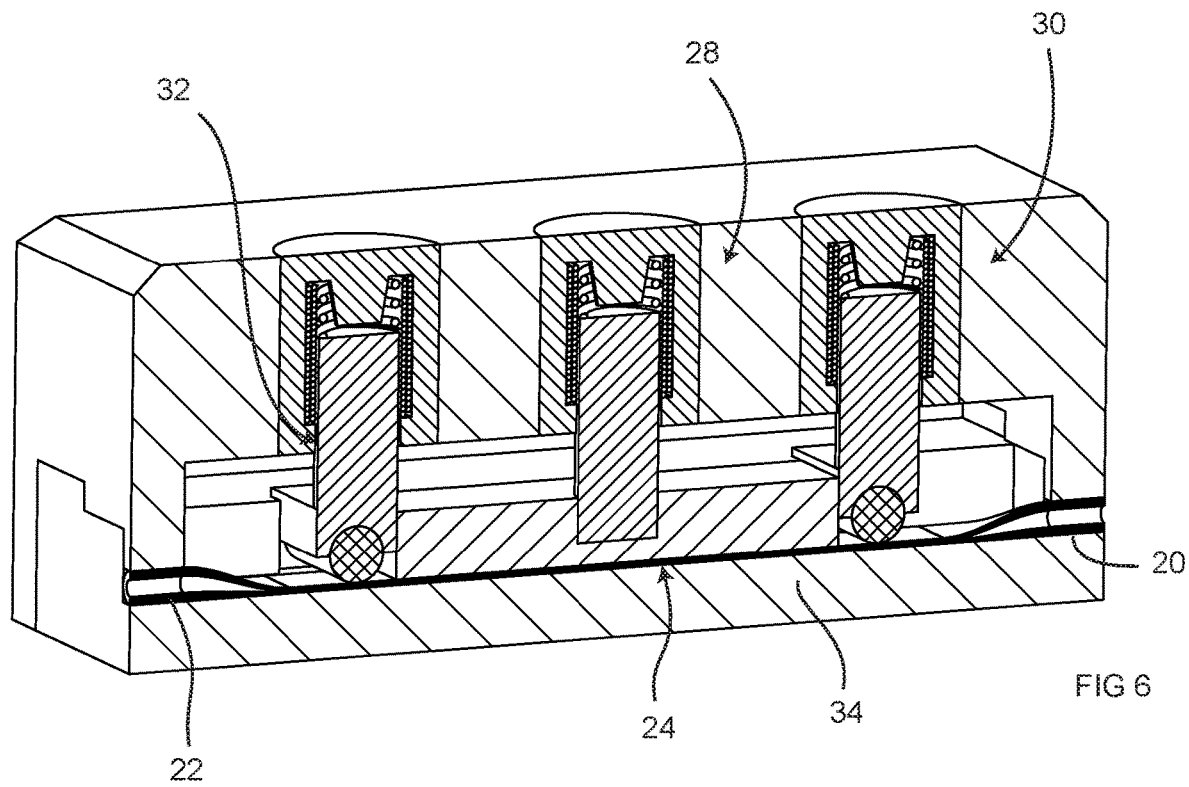

MICROPUMP

This application is the U.S. national phase of International Application No. PCT/IB2016/056870 filed Nov. 15, 2016, which designated the U.S. and claims priority to EP Patent Application No. 15195733.9 filed Nov. 20, 2015, the entire contents of each of which are hereby incorporated by reference.

The present invention relates to a pump system for pumping fluids, in particular a microfluidic pump system.

Microfluidic pump systems may be used in a variety of applications, for instance in medical applications or in fluid sampling applications. Microfluidic pumps typically have fluid flow rates in the range of $10 \times 10^{-9}$ liter per minute to $10 \times 10^{-3}$ liters per minute. In medical applications, microfluidic pumps may be used for administration of medicaments in liquid form to a patient. Microfluidic pumps may also be used in non-medical applications such as flow cytometry or other sampling or measurement applications. In many microfluidic applications, in particular medical applications, it is important to ensure sterility of the pumped liquid. In many applications, there is also an advantage in having a disposable pump system that is thrown away after a predefined action or state depending on the application, for instance: after a single administration, after a supply of medicament in a reservoir of the disposable part is empty, or after a specified time of administration (e.g. a few days).

One of the applications for a microfluidic pump system may for instance be for an infusion set for administration of a liquid medicament, for instance insulin. The infusion set may be provided in the form of a patch pump that is worn by the patient, the patch pump having disposable components.

There is an advantage in providing low cost disposable parts that meet high safety and sterility standards required.

It is further advantageous in micropumps to have a particularly accurate pumping volume for very small volumes in order of a few micro liters.

In conventional pump systems, there may be piston type of pumps in which a plunger is advanced in cylindrical reservoir. Other known pump systems comprise a rotating and axially movable rotor, or membrane type pumps. In order to ensure a high degree of accuracy in the pumped volume, especially for small quantities to be pumped, actuation means need to be made with a very high precision and are costly in conventional microfluidic pump systems. Moreover, in conventional pump systems having movable parts intervening in the pump chamber and thus requiring movable sealing means, safety and sterility are difficult to ensure reliably. Peristaltic type of pumps or shuttle pumps that have actuators pressing on an elastic tube, provide a high degree of sterility because the pump liquid is completely separated from the external environment, however the elastic tube is generally made of elastomer which have a restricted compatibility with drugs and are porous to gases. The elastomeric tubes require special coatings and are often costly to manufacture. For demanding applications the elastic properties of such tubes may vary over time and thus leading to a reduced accuracy.

GB2065789 discloses a shuttle type pump including upstream and downstream flexible conduits and first and second movable members operable for constricting and opening the conduits. A disposable cassette is disposed between the upstream and downstream conduits and comprises a rigid enclosure defining a pumping cavity. The enclosure is provided with a window and a flexible diaphragm closing the window and configured to cooperate with an actuator which is operated in sequence with respect to the first and second members in order to pump fluids from the upstream to the downstream conduits.

WO80/01934 discloses also a shuttle pump including a pump housing configured to receive and hold a disposable pump chamber. The disposable pump chamber comprises upstream and downstream conduits and contains two flexible rolling diaphragm chambers therebewteen which act as first and second pumping chambers which cooperate with first and second pistons respectively such as to pump fluids from the upstream to the downstream conduits.

The configuration of above pumps makes it difficult to provide a sterile pump which therefore may have restricted compatibility with the use of drugs. Moreover, to reach a good accuracy, these pumps must be calibrated each time a new cassette/pump chamber is loaded.

It is an object of this invention to provide a micropump for a microfluidic pump system that is very accurate, especially for very small pump volumes, and that is very reliable and sterile.

It is advantageous to provide a micropump for a microfluidic pump system that is that is easy to calibrate.

It is advantageous to provide a micropump for a microfluidic pump system that is cost effective to manufacture and thus convenient to integrate in a disposable device.

It is advantageous to provide a micropump for a microfluidic pump system that is safe and reliable for use in medical applications for administration of liquid drugs.

It is advantageous to provide a micropump for a microfluidic pump system that is very versatile, in particular that can be implemented in a wide range of applications.

It is advantageous to provide a micropump for a microfluidic pump system that can be easily calibrated.

It is advantageous to provide a micropump for a microfluidic pump system that may be used for pumping fluids without any risk of contamination or damage to the fluid due to the pumping system, for instance by avoiding moving parts or seals that separate the volume of liquid to be pumped and the external environment.

Objects of the invention have been achieved by providing a micropump according to claim 1, and a method of producing a micropump according to claim 15.

Disclosed herein is a micropump including a support structure, a pump tube, and an actuation system comprising one or more pump chamber actuators. The pump tube comprises a pump chamber portion defining therein a pump chamber, an inlet portion for inflow of fluid into the pump chamber, and an outlet portion for outflow of fluid from the pump chamber, the inlet, outlet and pump chamber portions forming part of a continuous section of tube made of a supple material. The one or more pump chamber actuators are configured to bias against the pump chamber portion to expel liquid contained in the pump chamber via the outlet portion, respectively to bias away from the pump chamber portion to allow liquid to enter the pump chamber via the inlet portion. The pump chamber portion has a cross-sectional area $A_p$ in an expanded state that is larger than a cross-sectional area $A_i$ of the pump tube at the inlet and outlet portions.

In an advantageous embodiment, the one or more pump chamber actuators may comprise one or more tube coupling interface elements fixed to one side of the pump chamber portion.

In an advantageous embodiment, the one or more tube coupling interface elements may be bonded to a wall portion of the pump chamber portion.

In an advantageous embodiment, the actuation system further comprises an inlet valve, and an outlet valve in the form of pinch valves that bias against the pump tube on an inlet, respectively outlet side of the pump chamber portion.

The inlet pinch valve may be operated by means of an inlet valve actuator and the outlet valve may be operated by means of an outlet valve actuator.

In an advantageous embodiment, the pinch valves bias against an expanded section of the pump chamber portion.

In an advantageous embodiment, the pinch valve actuators may be bonded to the pump tube.

In an advantageous embodiment, the inlet and outlet valves comprise an elastic body configured to apply elastic pressure closing together opposing surfaces of the pump chamber portion.

In an advantageous embodiment, the pump chamber actuator and/or the inlet valve actuator and/or the outlet valve actuator is/are passively driven in one direction by means of a spring element.

In an advantageous embodiment, the pump chamber actuator and/or the inlet valve actuator and/or the outlet valve actuator is/are actively driven in at least one direction by means of an electromagnetic actuator.

In advantageous embodiments, the ratio of the pump chamber portion cross-sectional area over the inlet and outlet portions cross-sectional area Ap/Ai is in a range of 4 to 100.

In advantageous embodiments, the ratio of the pump chamber portion cross-sectional area over the inlet and outlet portions cross-sectional area Ap/Ai may be more particularly in a range of 9 to 64.

In advantageous embodiments, the micropump is configured for pumping liquids in the range of 1 nl/min to 100 ml/min.

In advantageous embodiments, the micropump may be configured for pumping liquids more particularly in the range of 10 nl/min to 300 µl/min.

In an advantageous embodiment, the pump chamber portion is a blow molded section of polymer tube.

In an advantageous embodiment, the polymer is a thermoplastic polymer, for instance selected from Perfluoroalkoxy (PFA), Fluorinated ethylene propylene (FEP), or a fluoropolymer.

In an advantageous embodiment, opposed wall portions of the pump chamber portion are fixed to elements that form parts of the actuation system and housing that move relatively with respect to each other, configured to pull apart or press together the wall portions.

In an advantageous embodiment, the actuators may comprise position sensors configured to determine the state of operation of the pump.

In an advantageous embodiment, the position sensors may comprise capacitive sensors that detect the position of the biasing organ.

In a variant, the position sensors may comprise magnetic sensors that detect the position of the biasing organ.

Also disclosed herein is a method of manufacturing a micropump including a support structure, a pump tube, and an actuation system, the pump tube comprising a pump chamber portion defining therein a pump chamber, an inlet portion for inflow of fluid into the pump chamber, and an outlet portion for outflow of fluid from the pump chamber, wherein the inlet portion, outlet portion and pump chamber portion form part of a continuous section of tube made of a supple material, the method characterized by forming the pump chamber portion by blow molding.

In an advantageous embodiment, the method comprises flattening the pump chamber portion after the blowmolding step.

In an advantageous embodiment, the method comprises bonding opposed wall portions of the pump chamber portion to respective elements of the actuation system and housing that move relatively with respect to each other configured to pull apart or press together the wall portions.

Also disclosed herein is a microfluidic pump system for administering a liquid medication, comprising a reusable part including a drive unit and an electronic control system and a disposable part including a liquid supply system, a delivery system for administering the liquid medication to a patient, and a micropump as described above.

In an advantageous embodiment, the microfluidic pump system is configured in the form a patch pump comprising an adhesive surface for adhering to the skin of a patient for delivery of a liquid medication.

Further objects and advantageous features of the invention will be apparent from the claims, from the detailed description, and annexed drawings, in which:

FIG. 1a is a schematic simplified perspective view of a medical patch pump system according to an embodiment of the invention;

FIG. 1b is a schematic simplified perspective of the patch pump system of FIG. 1a showing separation of reusable and disposable parts;

FIG. 1c is a schematic simplified perspective cross-sectional view of the pump system of FIG. 1a;

FIG. 2a is a schematic simplified perspective view of a microfluidic pump system according to an embodiment of this invention;

FIG. 2d is a perspective cross-sectional view of a microfluidic pump system according to an embodiment of the invention;

FIG. 3a is a perspective view of a pump chamber portion of a microfluidic pump system according to an embodiment of the invention, the pump chamber portion being in an empty state;

FIG. 3b is a view similar to FIG. 3a with the pump chamber in a partially full state;

FIG. 4b is a cross-sectional view through lines G-G of FIG. 4a;

FIG. 4c is a cross-sectional view through line A-A of FIG. 4a;

FIG. 4d is a cross-sectional view through line B-B of FIG. 4a;

Figure 4A:
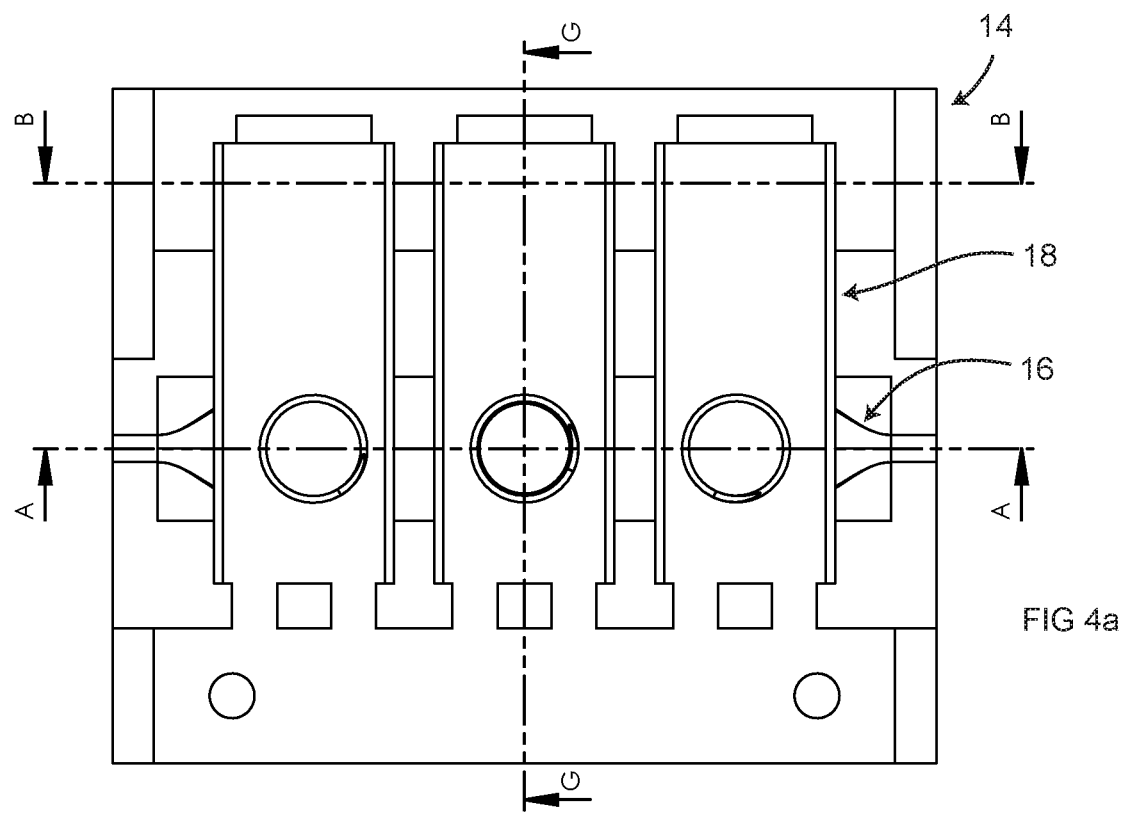
FIG. 4a is a top view of a microfluidic pump system with a portion of housing removed according to an embodiment of this invention.
Figure 4B:
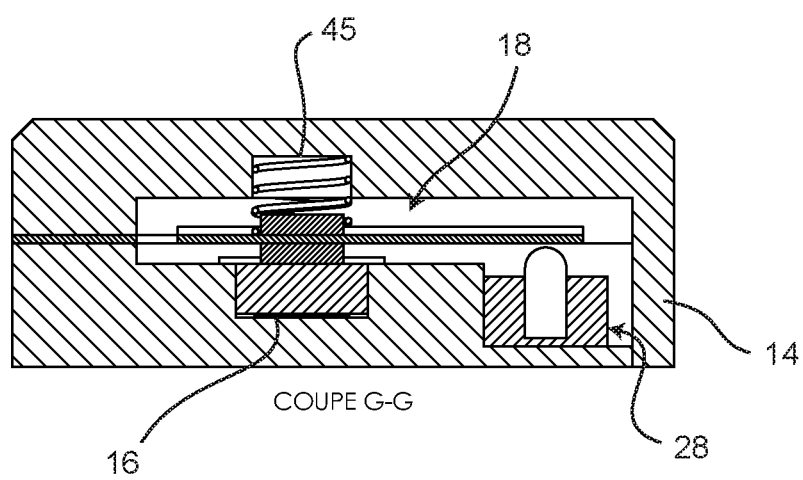
Figure 8:
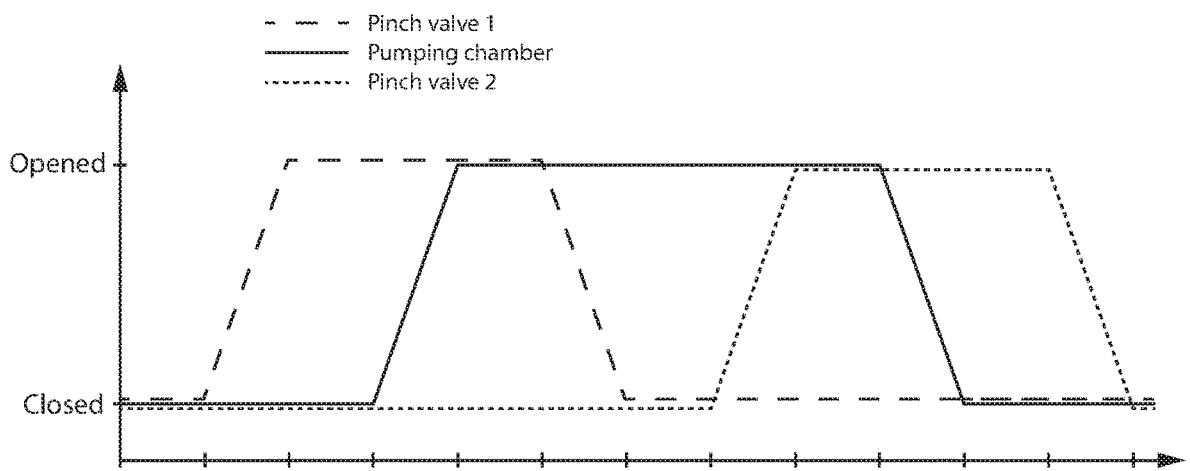
Figure 7:
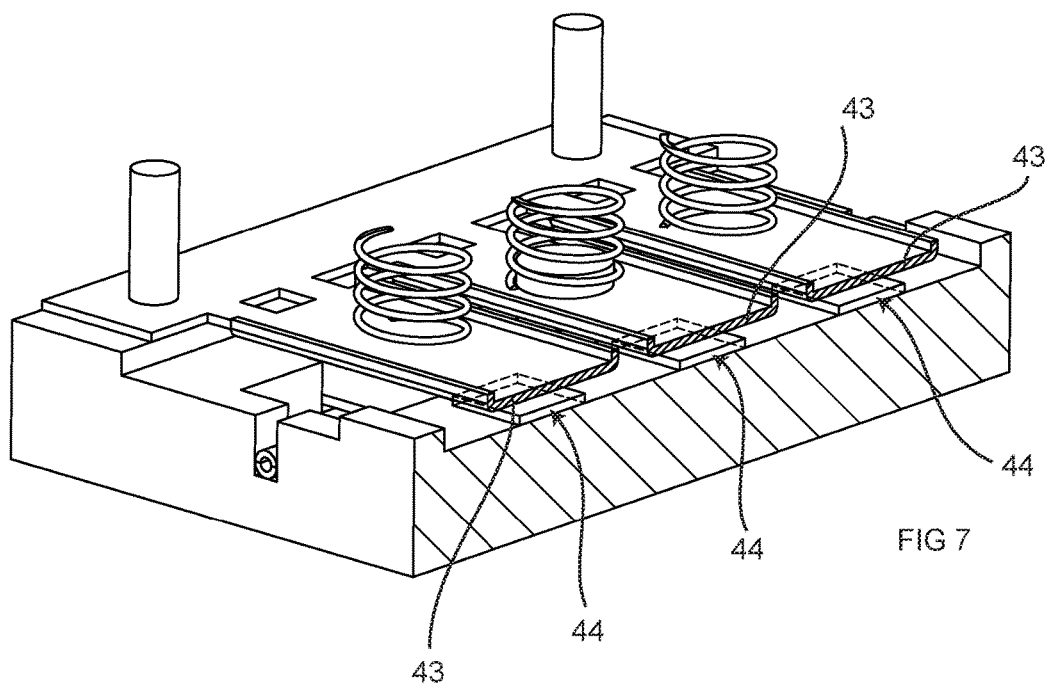

FIGS. 5a, 5c, 5e, 5g are similar to figure to FIG. 4c but showing the microfluidic pump system in different pumping stages whereby FIG. 4c shows the pump chamber in an empty state, FIG. 5a shows the inlet valve open and the pump chamber being filled, FIG. 5c shows the pump chamber full and the valves closed, FIG. 5e shows the outlet valve open and the pump chamber being emptied; and FIG. 5j shows the outlet valve about to be closed and the pump chamber just emptied;

FIGS. 5b, 5d, 5f, 5h are similar to FIG. 4d showing the position of actuators during the pumping steps illustrated in FIGS. 5a, 5c, 5e, 5j respectively;

FIG. 6 is schematic cross-sectional view of a microfluidic pump system according to another embodiment of the invention;

FIG. 7 is a perspective cross-sectional view with portions of housing removed of a microfluidic pump system according to an embodiment of this invention illustrating position sensors of actuating elements;

FIG. 8 is a graph schematically illustrating a pumping sequence and opening and closing of valves of a microfluidic pump system according to embodiments of the invention;

FIGS. 9a to 9d are simplified schematic perspective views illustrating steps in manufacturing a pump chamber portion of a microfluidic pump system according to an embodiment of the invention.

Referring to the figures, starting with FIGS. 1a to 1c, a microfluidic pump system 2 according to an embodiment of this invention is in the form of a pump system for administering medical liquids, comprising a reusable part 4 and a disposable part 6. The reusable part 4 includes a drive unit 5 and an electronic control system 7. The disposable part 6 includes a liquid supply system, for instance incorporating a liquid reservoir containing the medication to be administered, a delivery system 8 for administering the liquid to a patient, for instance incorporating a needle for subcutaneous administration of liquid or for feeding into a catheter, and a micropump 10 for pumping the liquid from the liquid reservoir to the delivery system 8.

The microfluidic pump system may for instance be in the form of a patch pump comprising an adhesive surface 3 for adhering to the skin of a patient for delivery of a medication over a few days to a few weeks. Patch pump systems are per se well known, for instance for administration of insulin to patients suffering from diabetes. In such systems it is well known to have a reusable part comprising a drive and electronics that may be reused multiple times with a plurality of disposable systems that are thrown away once removed from the patient or after the liquid in the reservoir is empty or nearly empty, or after a specified time.

A micropump 10 according to embodiments of this invention may advantageously be implemented in a disposable part of a patch pump configuration. A micropump 10 according to embodiments of the invention may however be implemented in many other systems requiring pumping of small quantities of liquids, particularly in the range of 10 nl/min ($10 \times 10^{-9}$ litres/minute) to 10 ml/min, more particularly in the range of 10 nl/min to 300 µl/min.

The micropump 10 according to embodiments of this invention comprises a housing or support structure 14, a pump tube 16, and an actuation system 18.

The pump tube 16 comprises a pump chamber portion 24 defining therein a pump chamber 26, an inlet 20 for inflow of fluid into the pump chamber, and an outlet 22 for outflow of fluid from the pump chamber. The inlet, outlet and pump chamber portion form part of a continuous section of tube made of a supple material, for instance a polymeric material such as Perfluoroalkoxy (PFA), Fluorinated ethylene propylene (FEP), a thermoplastic fluoropolymer or various other thermoplastic materials, the choice of which may depend inter alia on the intended application and need for compatibility with the liquid to be pumped.

In the figures, the inlet and outlet are shown with end faces however the inlet and outlet may continue with long sections of tube connected at their respective ends to a delivery system respectively a liquid supply reservoir. The section of tube may be provided without interruptions such that the pump chamber portion 24 is connected to the liquid supply and delivery system by respective connectors at the liquid supply system and delivery system respectively. This ensures, similar to peristaltic type of pump systems, a continuous flow of liquid within the pump system separated from the external environment by a continuous wall without the need for sealed moving parts separating the liquid to be pumped from the external environment. This ensures a high degree of sterility in the separation of the liquid to be pumped from the external environment.

Figure 9A:
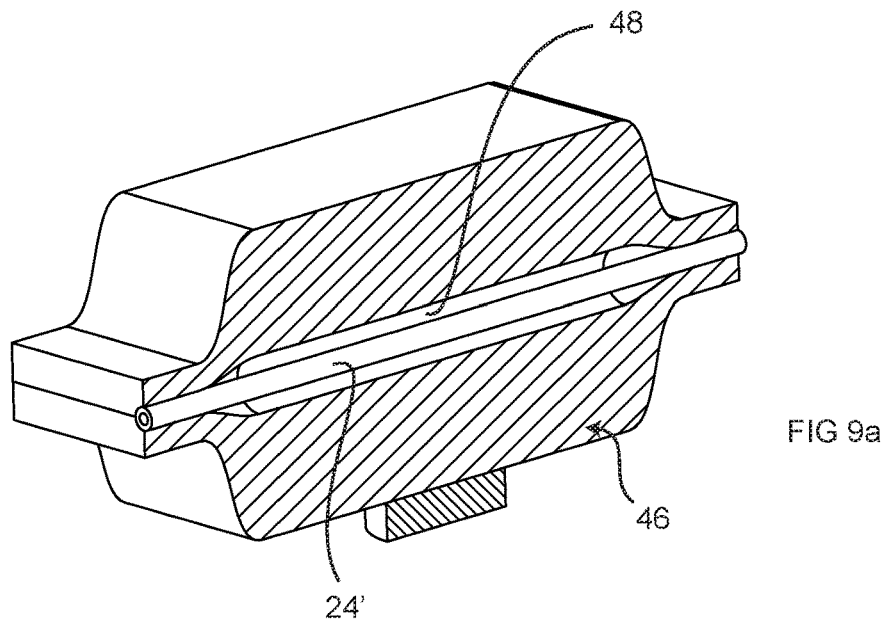
Figure 9B:
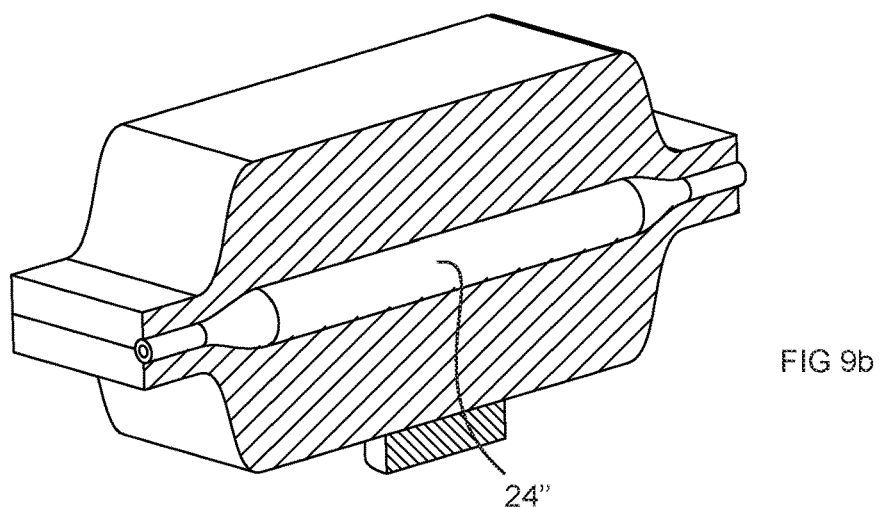
Figure 9C:
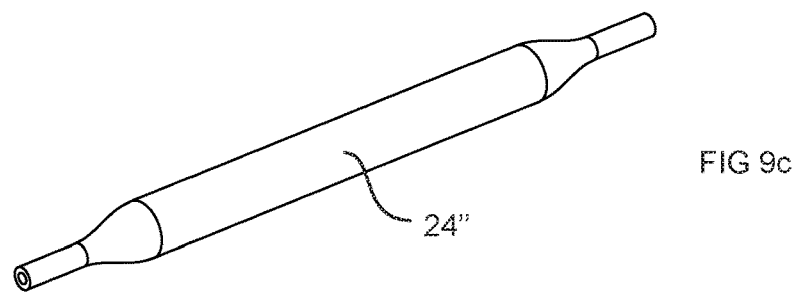
Figure 9D:
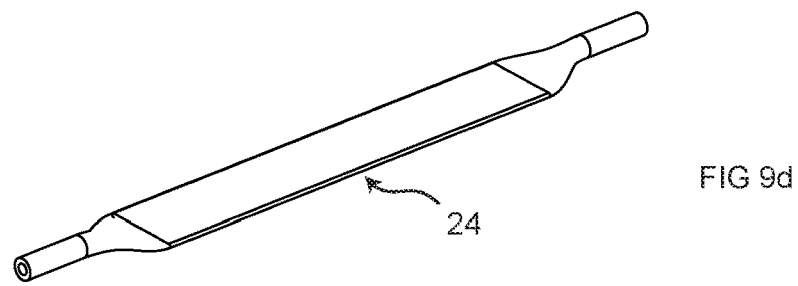

Referring to FIGS. 9a to 9d, the pump chamber portion 24 may be advantageously manufactured by a blow molding process. As illustrated in FIG. 9a, a section of polymer tube 24' is placed within a die 46 comprising a cavity 48 configured to form the pump chamber portion. As is per se known in blow molding processes, the section of polymer 24' is heated and gas pressure is applied within the tube so that it expands outwardly until the tube contacts and conforms to the chamber 48 in the die. The die may then be opened and the section of tube removed. In a subsequent step, the expanded blow molded section 24 may then be flattened to form the pump chamber portion 24 for assembly within the housing of the micropump.

The volume of the pump chamber 28 formed within the pump chamber portion 24 may be varied for the pumping operation by pulling apart the opposed flattened wall portions 24a, 24b of the pump chamber portion 24 to increase the volume therein, or by pressing together the opposite wall portions 24a, 24b to expel fluid out of the pump chamber. The blow molded pump chamber portion 24 is particularly cost effective to manufacture while at the same time ensuring a very high level of reliability and safety from contamination. Moreover, contrary to peristaltic or shuttle type of pumps, the pumping action does not rely on the inherent elasticity of the tube and is not limited to the initial diameter of the tube.

In the present invention, the tube section as shown by the illustrated inlets and outlets 20, 22, can have a very small diameter $D_i$ relative to the pump chamber portion diameter $D_p$. The ratio of diameters $D_p/D_i$ may advantageously be in a range of 2 to 10, preferably in range of 3 to 8. The relatively small tube reduces the dead volume of liquid between the liquid supply and micropump, respectively from the micropump to the delivery system, while at the same time allowing to pump a volume of liquid defined by the expanded pump chamber portion 24 that has a diameter $D_p$ that may be 2 to 8 times or more the diameter $D_i$ of the inlet and outlet portions of the tube. The actual amount of liquid to be pumped may be controlled by the degree of separation of the opposite wall portions 24a, 24b thus defining the volume of the pump chamber therebetween as well as the number of inflow and outflow (pumping) cycles. Within the scope of the invention, the tube original shape may not necessarily be a circular or essentially circular shape in cross-section, an may have a variety of other cross-sectional profiles such as square, polygonal, elliptical and various irregular profiles. More generally, in advantageous embodiments, the ratio of the pump chamber portion cross-sectional area (in its fully expanded operational state) over the inlet and outlet portions cross-sectional area Ap/Ai is in a range of 4 to 100, more preferably in a range of 9 to 64.

In order to effect the pumping operation, the opposed wall portion 24a, 24b of the pump chamber portion 24 are fixed to elements that form parts of the actuation system and housing that move relatively with respect to each other to pull apart or press together the wall portions 24a, 24b.

Figure 2B:
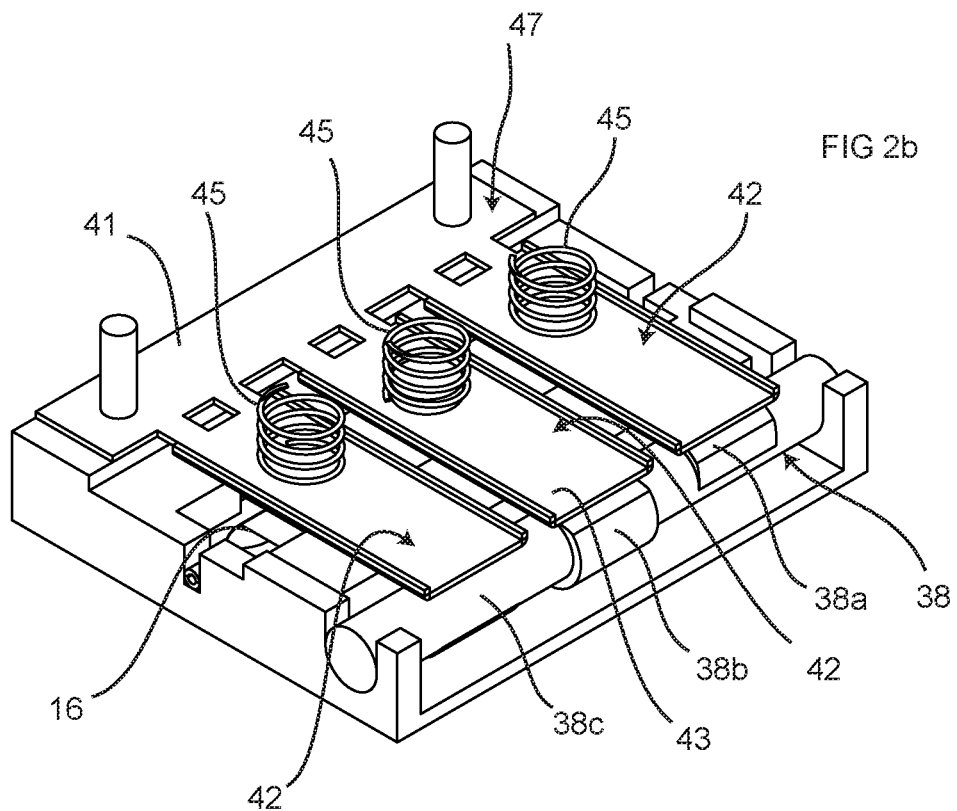
FIG. 2b is a perspective view of a microfluidic pump system according to an embodiment of this invention with a portion of housing removed.
Figure 2C:
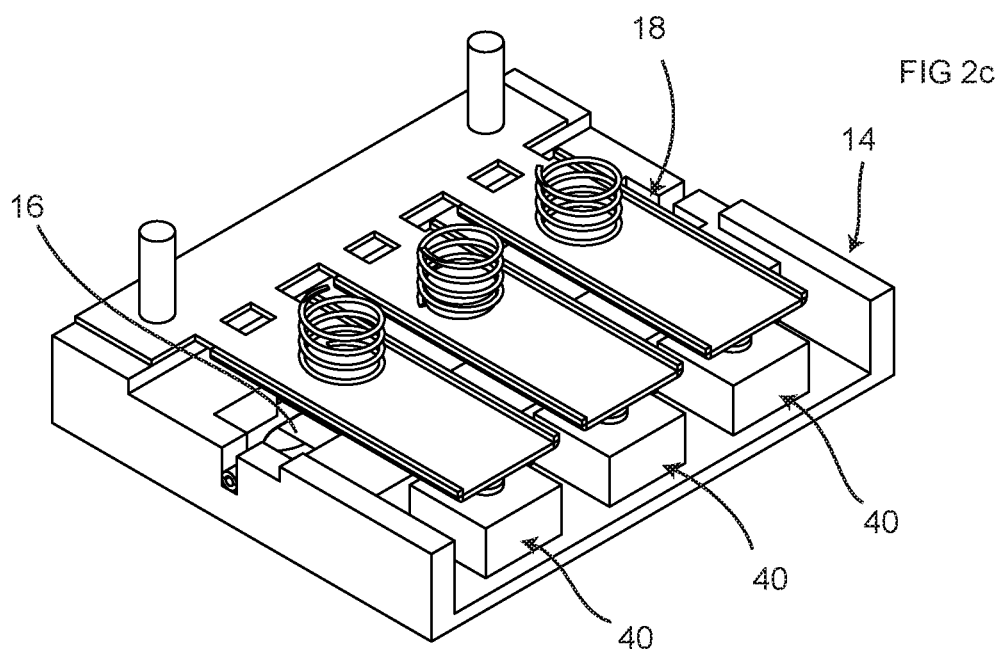
FIG. 2c is a view similar to FIG. 2b but of another embodiment according to the invention.

In the embodiment illustrated in FIG. 2d, a surface portion 25 of the upper wall portion 24a of the pump chamber portion 24 is fixed to a tube coupling interface element 34 of a pump chamber actuator 28 of the actuation system 18 whereas the opposite side 24b is fixed to a base wall 14b of the housing 14. The fixing means between the housing and wall portion 24b, respectively between the interface element 34 and wall portion 24a of the pump chamber portion 24 may be by welding, brazing, adhesive bonding, cold or hot heading or various other per se known bonding techniques between materials, in particular the polymeric material of the pump chamber portion and material of the housing interface element. The interface element and housing may also be made of a polymeric material, for instance injected plastic of similar or different polymer than that of the tube section, although non-polymeric materials may also be used depending on the applications, provided that fixing technique is also adapted for the pair of materials used. Welding may for instance be performed by known techniques such as ultrasonic welding or laser welding.

In an advantageous embodiment, the pinch valve actuators 31, 33 may be bonded to the pump tube 16, in particular to ends of the pump chamber portion 24. The bonding of the pinch valve actuators to the pump tube may be by welding, brazing, adhesive bonding, cold or hot heading or various other per se known bonding techniques between materials in a similar manner than the pump chamber actuator bonded to the pump chamber portion. This allows to use a non-elastic material for the pump tube 16 yet ensure that the pinch valve actively opens the tube sufficiently to ensure low fluidic resistance when opened. The active drawing in of liquid into the pump chamber confers an important advantage, in particular in the case of an underpressure upstream (e.g. in the reservoir), or for pumping viscous fluids.

The actuation system 18 comprises one or more pump chamber actuators 28 comprising one or more tube coupling interface elements 34 fixed to one side of the pump chamber portion 24, an inlet valve 30, and an outlet valve 32. In a preferred embodiment the inlet and outlet valves 30, 32 are in the form of pinch valves that bias against the pump tube 16 on the inlet and outlet side of the pump chamber portion 24. In an advantageous embodiment, the pinch valves bias against the expanded section of the pump chamber portion 24. In a variant however, the pinch valves may also pinch the tube sections outside of the expanded portion, on the tube sections that are not expanded (i.e. not blow molded).

The inlet and outlet valves 30, 32 may advantageously comprise an elastic body, for instance made of an elastomer, configured to apply elastic pressure closing together the opposing surfaces of the pump chamber portion while reducing local pressure to avoid damage to the pump tube 16 while ensuring a good pinch sealing of the valve.

The inlet pinch valve 30 is opened and closed by means of a pinch valve actuator 31. The outlet valve may be operated by means of an outlet valve actuator 33.

In a variant, the outlet valve actuator may be a passive actuator that is spring biased such that the outlet valve pinches the tube in a closed position during inflow of liquid in the pump chamber portion when the inlet valve is open. In the latter variant, the outlet valve biases open under pressure of the liquid within the pump chamber when the inlet valve is closed and the pump chamber actuator is actuated to reduce the volume in the pump chamber portion.

In a variant, the inlet and outlet valves may be provided at the liquid supply system, respectively the needle actuation system, rather than at the entry and exit of the micropump 10.

The pump chamber actuator 28 and pinch valve actuators 31, 33 may have similar configurations or may have different actuating mechanisms. In embodiments shown, the actuation system comprises a biasing mechanism 47 with springs 45 that bias both inlet and outlet pinch valves as well as the interface element 34 of the pump chamber actuator 28 to the closed position, as best illustrated in FIG. 2d or 6 where the pump chamber 26 is empty and the pinch valves closed. This configuration provides a fail safe mode whereby in case of loss of power or failure of the actuation system, fluid flow between liquid supply system and delivery system is closed. Such fail safe mode is useful in many applications, for instance in medical applications. Nevertheless, for certain applications that may require fluid connection between the fluid supply and the delivery system to remain open, the fail safe mode or power off mode may require the springs to bias the biasing mechanism 47 to an open position where both the inlet and outlet valves are open and the interface element 34 of the pump chamber actuator is in a raised position to allow liquid to flow through the pump chamber.

In embodiments with a spring biasing mechanism to the open or the closed position as needed by the system, the actuation system comprises a drive mechanism that acts in the direction opposite to the spring biasing force to effect the opposite action. In the embodiment illustrated in FIG. 2b, the interface element drive 36 of the pump chamber actuator 38 is provided in the form of a rotating camshaft 38. The rotating camshaft comprises a cam profile portion 38b that, in opposition to the spring force, raises and lowers the biasing organ 42 coupled to the interface element 34 to increase, respectively decrease the volume in the pump chamber as a function of the angle of rotation of the cam. The rotating cam may be turned by an electrical motor directly or through a reduction gearing system or by other known electrical actuation means for rotating a component. The camshaft 38 may be provided with cam profile portions 38a, 38c for actuating the pinch valves in a similar manner as a function of rotation of the camshaft. In this embodiment, the opening and closing of the pinch valves and raising and lowering of the pump chamber interface element are thus directly mechanically synchronised and the pumping volume per rotation of camshaft is a fixed amount.

While in the aforegoing it is mentioned that the inlet is connected to a liquid supply system and outlet connected to a delivery system, the micropump according to embodiments of the invention may be made as a bi-directional pump and therefore an inlet may act also as an outlet and an outlet as an inlet for flow of liquid in both directions depending on the order of opening and closing of the pinch valves and actuation of the pump chamber portion. Using a rotating cam this may be done for instance by simply reversing the direction of movement of the rotating cam. A reverse flow of liquid may for instance be implemented in certain applications to provide a drawback of liquid from the delivery system to the supply system or for connection between two liquid supply systems for mixing or other operations.

In the illustrated embodiments, the biasing mechanism 47 is in the form of a leaf spring plate with cantilever arms 43 that are pivotally connected to a base portion 41, the spring biasing force acting on the spring arms 43 being provided by coil springs 45. In other possible variants, various other spring mechanisms may be used that are per se well known to the skilled person. Also, the spring force may be provided by the cantilever arms 43 due to their inherent elasticity without the use of additional coil springs or other additional springs.

In the illustrated embodiments, the pinch valves and interface element of the pump chamber actuator are positioned on a portion of the arm that is intermediate the base 41 and free end 43 of the arms, the actuators being positioned proximate the free end 43 of the arms. The actuation of the spring arms 42 may thus be effected with a larger displacement than the actual displacement of the pinch valve, respectively pump chamber actuators, thus increasing the control and accuracy of the variation of volume in the pump chamber 26.

In another embodiment, instead of a rotating cam, each of the biasing organs 42 of the pump chamber actuator 28 and the inlet and outlet valves 30, 32 may be effected by other individual actuation means such as linear actuators for instance in the form of solenoids as illustrated in the embodiment of FIG. 6 or by piezo electric actuators.

In variants, the actuation means may be provided by other per se well known actuators such as pneumatic or hydraulic actuators, or other forms of electromagnetic actuators.

In a variant, instead of acting against spring means, the actuators may also effect forward and reverse movements without spring means to effect the pump chamber volume variation and opening and closing of valves. The actuators may effect the forward and reverse movements actively, or in a variant, actively in one direction and passively in the other by the force of the spring means. Spring means may also be integrated within the actuators to effect the passive movement in one direction.

In using individual actuators 40, the displacement of each actuator may have a fixed displacement travel similar to the cam operation of the biasing organ. In a variant, the pump chamber actuator 28 may have a variable travel that may be controlled in order to change, as needed, the pumping volume per cycle.

The actuators may further be provided with position sensors 44 (see FIG. 7) for instance in the form of capacitive sensors that detect the height of the biasing organ 42, for instance the position of the free ends 43 of the biasing organ, for the pump chamber and for the pinch valves in order to determine the state of operation of the pumping. The position sensors may also be used to determine a malfunction in the pump, in particular malfunction of the pinch valves or the pump chamber actuator. The sensors may also be used to determine or to control the pumping operation in particular the pumping volume rate.

Referring to FIGS. 4c to 5h and FIG. 8, a pumping cycle according to embodiments of the invention is illustrated. As shown in FIG. 4c, the inlet pinch valve is opened by the inlet valve actuator 31 and then the pump chamber actuator 28 is raised to increase the volume in the pump chamber 26 as shown in FIGS. 5a and 5b. The inlet valve is then closed as shown in FIGS. 5c, 5d and then the outlet valve is opened as shown in FIGS. 5e and 5f and the pump chamber actuator 28 is depressed until the liquid is expelled as shown in FIGS. 5g and 5h. The outlet valve may then be closed and a pump cycle repeated.

As mentioned previously, the outlet valve can be actively actuated by a motorized actuation element or may be passive in the sense of being a spring biased pinch valve that opens due to the pressure of the liquid in the pump chamber when the pump chamber actuator is depressed.

The micropump can be in different manners to create a flow. For instance, in an embodiment, the fluid flow is a sequence of discrete amounts, by successively repeating complete pumping cycles, thus the flow is given by the pumped volume per cycle and its frequency. A time delay can be introduced between pumping cycles. Another possibility is to create a continuous flow by first filling the pumping chamber through the inlet and then expelling the fluid by the compression of the pumping chamber over a certain time (push). Alternatively the pumping chamber can be filled over a certain time to create a continuous flow (pull). These operations may be repeated and/or combined in any chosen sequence.

---

List of references used

Pump system 2 (e.g. patch pump)
    adhesive base 3
reusable part 4
    drive unit 5
    control system 7
disposable part 6
    delivery system 8 (e.g. needle system)
    liquid supply system 12
        e.g. liquid reservoir
    micropump 10
        housing/support 14
        pump tube 16
            inlet 20
            outlet 22
            pump chamber portion 24
                attachment surface portion 25
                pump chamber 26
    actuation system 18
        inlet valve 30
            pinch valve
                elastic body
        outlet valve 32
            pinch valve
                elastic body
        pump chamber actuator(s) 28
            tube coupling interface, element 34
            interface element drive 36
                1st embodiment
                rotating cam 38
                biasing mechanism 47
                (leaf spring plate & springs)
                spring biasing organ 42
                      pivot arm -> leaf spring arm
                          base portion 41
                          free end 43
                      compression spring 45
                2nd embodiment
                linear actuators 40
                spring biasing organ 42
                3rd embodiment
                linear actuators 40
                no spring for return
                (active two way displacement)
            position sensor(s) 44
blow molding die 46
    chamber 48

The invention claimed is:

1. A micropump including a support structure, a pump tube, and an actuation system comprising one or more pump chamber actuators comprising a camshaft and first and second cantilever arms, the pump tube comprising a pump chamber portion defining therein a pump chamber, an inlet portion for inflow of liquid into the pump chamber, and an outlet portion for outflow of liquid from the pump chamber, an adhesive surface configured to adhere to skin of a patient, the outlet portion coupled to a needle for subcutaneous administration of liquid to the patient having the micropump adhered thereto via the adhesive surface, the inlet portion, the outlet portion, and the pump chamber portion monolithically forming part of a continuous section of tube made of a supple material, the pump chamber portion bonded to a wall within the support structure via welding, brazing, adhesive bonding, or cold or hot heading, the first cantilever arm configured to cause, responsive to a spring force provided by the first cantilever arm and rotation of the camshaft, the pump chamber portion to expel liquid contained in the pump chamber via the outlet portion to the needle for subcutaneous administration to the patient, the second cantilever arm configured to allow liquid to enter the pump chamber via the inlet portion responsive to rotation of the camshaft, wherein the pump chamber portion has a cross-sectional area $A_p$ in an expanded state that is larger than a cross-sectional area $A_i$ of the pump tube at the inlet portion and the outlet portion, wherein an end of the inlet portion forms an inlet of the micropump and an end of the outlet portion forms an outlet of the micropump.

2. The micropump of claim 1, wherein the one or more pump chamber actuators comprise one or more tube coupling interface elements.

3. The micropump of claim 1, wherein the actuation system further comprises an inlet valve and an outlet valve in the form of pinch valves that bias against the pump tube on an inlet side and an outlet side of the pump chamber portion, respectively, the inlet pinch valve being operated by movement from an inlet valve actuator and the outlet pinch valve being operated by movement from an outlet valve actuator.

4. The micropump of claim 3, wherein the pinch valves bias against an expanded section of the pump chamber portion.

5. The micropump of claim 3, wherein the inlet pinch valve and the outlet pinch valve each comprise an elastic body configured to apply elastic pressure closing together opposing surfaces of the pump chamber portion.

6. The micropump of claim 3, wherein the inlet and outlet valve actuators individually actuate the inlet and outlet pinch valves, respectively, responsive to corresponding movement at the inlet and outlet valve actuators.

7. The micropump of claim 3, wherein the one or more pump chamber actuators and/or the inlet valve actuator and/or the outlet valve actuator is/are passively driven in one direction.

8. The micropump of claim 3, wherein the one or more pump chamber actuators and/or the inlet valve actuator and/or the outlet valve actuator is/are actively driven in at least one direction by an electromagnetic actuator.

9. The micropump of claim 8, wherein a ratio of the pump chamber portion cross-sectional area over the inlet and outlet portions cross-sectional area $A_p/A_i$ is in a range of 4 to 100.

10. The micropump of claim 9, wherein the micropump is configured for pumping liquids in a range of 1 nl/min to 100 ml/min.

11. The micropump of claim 3, wherein the one or more pump chamber actuators and/or the inlet valve actuator and/or the outlet valve actuator comprise position sensors configured to determine a state of operation of the micropump.

12. The micropump of claim 11, wherein the position sensors comprise capacitive and/or magnetic sensors that detect a position of a biasing organ.

13. The micropump of claim 1, wherein the pump chamber portion of the pump tube is a blow molded section of polymer tube.

14. The micropump of claim 1, wherein opposed wall portions of the pump chamber portion are fixed to elements that form parts of the actuation system and the support structure that move relatively with respect to each other, to pull apart or press together the wall portions.

15. A microfluidic pump system for administering a liquid medication, the microfluidic pump system comprising a reusable part including a drive unit and an electronic control system and a disposable part including a liquid supply system, a delivery system for subcutaneously administering the liquid medication to the patient, and the micropump of claim 1 for pumping the liquid from a liquid reservoir to the delivery system.

16. The microfluidic pump system of claim 15, configured in the form a patch pump for delivery of the liquid medication.

17. The micropump of claim 1, wherein the micropump is configured to pump insulin for subcutaneous administration to the patient.

18. The micropump of claim 1, wherein the pump chamber portion is bonded to the wall within the support structure via welding.

19. The micropump of claim 18, wherein the pump chamber portion is bonded to the wall within the support structure via laser welding.

20. The micropump of claim 1, wherein the first and second cantilever arms are configured to independently move, responsive to the spring force provided by the first cantilever arm and a spring force provide by the second cantilever arm respectively, relative to the pump tube.

21. The micropump of claim 20, wherein the one or more pump chamber actuators further comprise a third cantilever arm configured to move, response to a spring force provided by the third cantilever arm, relative to the pump tube.

22. The micropump of claim 20, wherein each of the first and second cantilever arms comprises an elongated, flat portion.

23. A micropump including a support structure, a monolithic blow-molded pump tube, and an actuation system comprising a camshaft, a first cantilever arm, and a second cantilever arm, an adhesive surface configured to adhere to skin of a patient, the monolithic blow-molded pump tube consisting of a continuous piece of tube made of a supple material and a pump chamber portion defining a pump chamber, an inlet portion, and an outlet portion coupled to a needle for subcutaneous administration of liquid to the patient having the micropump adhered thereto via the adhesive surface, the first cantilever arm configured to cause, responsive to a spring force provided by the first cantilever arm and rotation of the camshaft, the pump chamber portion to expel liquid contained in the pump chamber via the outlet portion to the needle for subcutaneous administration to the patient, the second cantilever arm configured to allow liquid to enter the pump chamber via the inlet portion responsive to rotation of the camshaft, wherein the pump chamber portion has a cross-sectional area $A_p$ in an expanded state that is larger than a cross-sectional area $A_i$ of the pump tube at the inlet and outlet portions.

24. The micropump of claim 23, wherein the pump chamber portion is bonded to a wall within the support structure via welding, brazing, adhesive bonding, or cold or hot heading.

25. The micropump of claim 24, wherein the pump chamber portion is bonded to the wall within the support structure via laser welding.

26. The micropump of claim 23, wherein each of the first and second cantilever arms comprises an elongated, flat portion, and
wherein the second cantilever arm allows liquid to enter the pump chamber responsive to a spring force provided by the second cantilever arm.

27. The micropump of claim 23, further comprising a third cantilever arm configured to move relative to the pump tube.

\* \* \* \* \*